United States Patent [19]

Lis

[11] Patent Number: 5,318,975

[45] Date of Patent: Jun. 7, 1994

[54] 5-PYRIMDINEAMINE DERIVATIVES

[75] Inventor: Randall E. Lis, Stanhope, N.J.

[73] Assignee: Berlex Laboratories, Inc., Cedar Knolls, N.J.

[21] Appl. No.: 17,895

[22] Filed: Feb. 16, 1993

[51] Int. Cl.$^5$ ............... C07D 403/12; C07D 403/14; A61K 31/505
[52] U.S. Cl. .................................. 514/275; 544/322; 544/331; 514/256
[58] Field of Search ............... 544/322, 331; 514/256, 514/275

[56] References Cited

U.S. PATENT DOCUMENTS 4,849,424  7/1989  Ikeda et al. .................... 514/256

Primary Examiner—John M. Ford
Attorney, Agent, or Firm—Elizabeth A. Bellamy; John L. White; Anthony J. Zelano

[57] ABSTRACT

This invention relates to novel 5-pyrimidineamine derivatives. The compounds of the invention exhibit cardiovascular properties, particularly mixed vasodilative, selective venous and arterial dilation. Pharmaceutical compositions are proposed for the compounds.

11 Claims, No Drawings

5-PYRIMDINEAMINE DERIVATIVES

SUMMARY OF THE INVENTION

This invention relates to novel 5-pyrimidineamine derivatives. The compounds of the invention exhibit a variety of pharmacological properties for which pharmaceutical compositions are proposed.

GENERAL DESCRIPTION OF THE INVENTION

COMPOSITION-OF-MATTER ASPECT

In its composition-of-matter aspect, this invention relates to novel 5-pyrimideamine derivatives.

Compounds encompassed by the invention are of the following formula I:

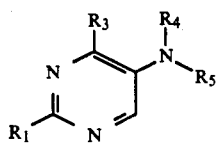

wherein, $R_1$ is hydrogen or

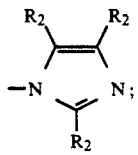

$R_2$ are the same or independently hydrogen or lower alkyl;

$R_3$ is hydrogen or lower alkyl;

$R_4$ is

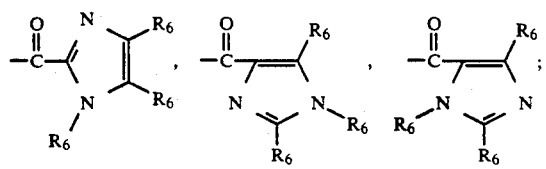

$R_5$ is hydrogen or $R_4$ and $R_6$ are the same or independently hydrogen, lower alkyl or benzyl.

As used herein the term lower alkyl shall represent a straight or branched chain alkyl of one to four carbon atoms as for example, methyl, ethyl, propyl, isopropyl, butyl, secbutyl, isobutyl and tertiary butyl.

It is understood that the definition of the compounds of Formula I encompasses the geometrical and optical isomers and racemic modifications thereof which possess the indicated activity.

It is also to be understood that the definition of the compounds of Formula I encompasses all possible polymorphic modifications and other solid state modifications which possess the stated activity.

The compounds which follow are some of those which serve to exemplify various aspects of the invention described herein.

A) N-(4-i-Propyl-5-pyrimidinyl)-1-(phenylmethyl)-1H-imidazol-2-yl-carboxamide.

B) N-(4-i-Propyl-5-pyrimidinyl)-1H-imidazol-2-yl-carboxamide.

C) N-(4-n-Butyl-5-pyrimidinyl)-1-(phenylmethyl)-1H-imidazol-2-yl-carboxamide.

D) N-(4-n-Butyl-5-pyrimidinyl)-1H-imidazol-2-yl-carboxamide.

E) N-(5-Pyrimidinyl)-1-(phenylmethyl)-1H-imidazol-2-yl-carboxamide.

F) N-(5-Pyrimidinyl)-1H-imidazol-2-yl-carboxamide.

G) N-[[2-(2-Ethyl-4-methyl-1H-imidazol-1-yl)]pyrimidin-5-yl]-1-(phenylmethyl)-1H-imidazol-2-yl-carboxamide.

H) N-[[2-(2-Ethyl-4-methyl-1H-imidazolyl-1-yl)pyrimidin-5-yl]-1H-imidazol-2-yl-carboxamide.

I) N-[[4-i-Propyl-2-(2-ethyl-4-methyl-1H-imidazol-1-yl)]pyrimidin-5-yl]-1-(phenylmethyl)-1H-imidazol-2-yl-carboxamide.

J) N-[[4-i-Propyl-2-(2-ethyl-4-methyl-1H-imidazol-1-yl)]pyrimidin-5-yl]-1H-imidazol-2-yl-carboxamide.

K) N-[[4-n-Butyl-2-(2-ethyl-4-methyl-1H-imidazol-1-yl)]pyrimidin-5-yl]-1-(phenylmethyl)-1H-imidazol-2-yl-carboxamide.

L) N-[[4-n-Butyl-2-(2-ethyl-4-methyl-1H-imidazol-1-yl)]pyrimidin-5-yl]-1H-imidazol-2-yl-carboxamide.

PROCESS ASPECT

In general, the compounds of the invention may be prepared by various reactants and processes known in the art. Illustrative but not limiting as the reactants and processes utilized for the preparation of the compounds of the invention are the following schemes A and B.

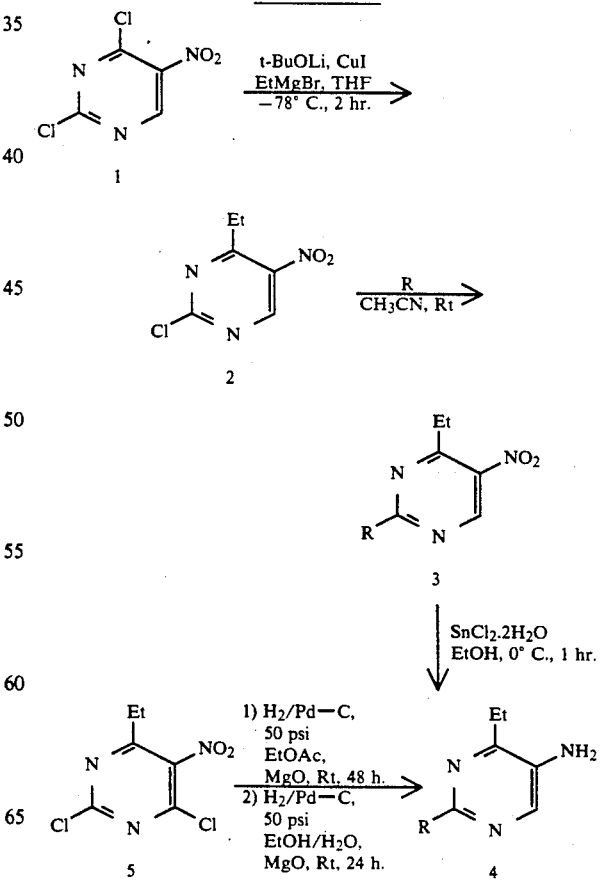

In the above Scheme A, R can be

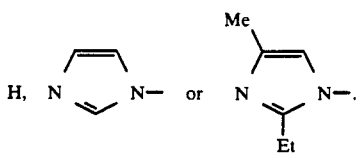

In Scheme A, reaction of 2,4-dichloro-5-nitropyrimidine (1) with lithium t-butoxide, cuprous iodide and ethylmagnesium bromide in THF at −78° C. gives 2-chloro-4-ethyl-5-nitropyrimidine (2). Displacement of the 2-chloro group in 2, is accomplished by treatment with 2-ethyl-4-methylimidazole or imidazole in acetonitrile at room temperature. Reduction of the nitro moiety in 3 to produce 4 is accomplished as illustrated. Reduction of 2,6-dichloro-4-ethyl-5-nitropyrimidine (5) is accomplished as illustrated to produce the compound 4 where R is hydrogen.

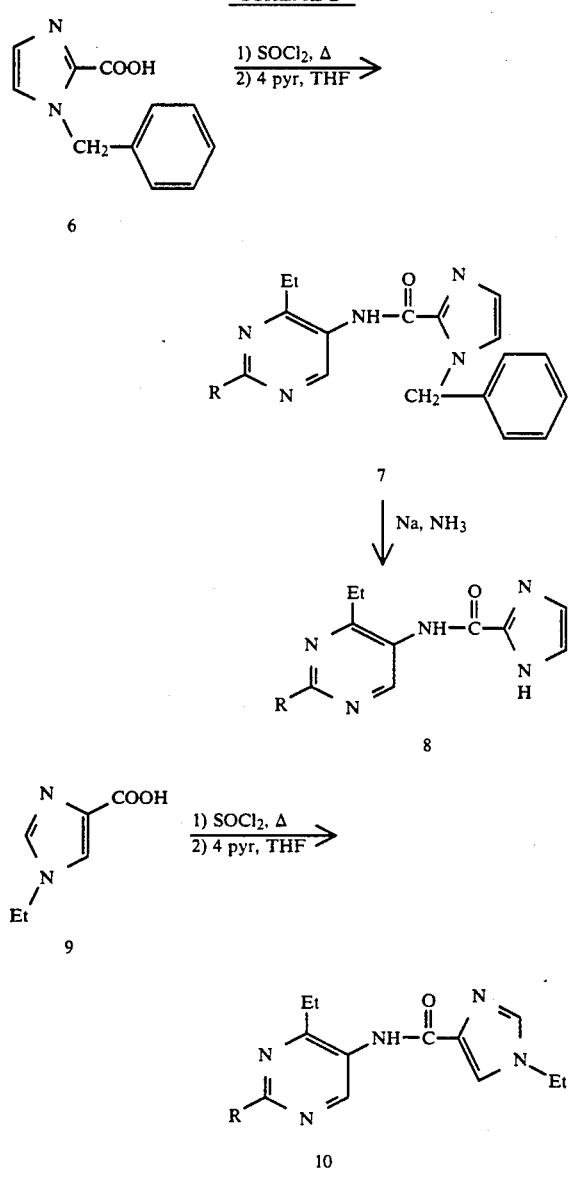

In the above Scheme B, R can be

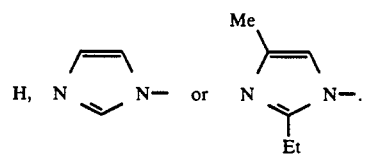

Compound 6 1-(phenylmethyl)-1H-imidazole-2-carboxylic acid, is treated with thionyl chloride to afford the corresponding acid chloride, which in turn is reacted with the appropriate amine 4 in pyridine and THF to produce the compound 7. Removal of the benzyl group in 7 via sodium and liquid ammonia produces compound 8. Compound 9 by illustrated fashion can be reacted to the appropriate compound 10.

METHOD OF USE AND PHARMACEUTICAL COMPOSITION ASPECT

The compounds of this invention have generally been found to exhibit cardiovascular effects. More especially they have been found to be vasodilator agents with some exhibiting selective vasodilator action. Furthermore, among the selective vasodilators they are distinguishable as mixed (arterial and venous) vasodilators, selective venodilators and selective coronary artery dilators. The selective vasodilators with a mixed profile for reduction of preload and afterload on the heart have utility in congestive heart failure; in addition, such agents have utility in the treatment of angina pectoris, hypertension and other disorders of the circulation. Selective venodilators which decrease the pre-load on the heart have utility in the treatment of angina pectoris and congestive heart failure. Selective coronary dilators have utility in certain forms of angina pectoris and other coronary vessel related diseases.

The following procedure was used for the initial identification of compounds having vasodilator activity. Such compounds would be useful for the treatment of hypertension or heart failure. The compounds were evaluated by assessing vasodilator activity in rings of canine coronary artery and mesenteric vein in vitro.

Dogs of either sex were anesthetized with pentobarbital (35 mg/kg, i.v.). The heart and mesentery were removed and placed in oxygenated (95% $O_2$/5% $CO_2$) physiological salt solution (PSS) at 37° C. The circumflex coronary artery and the mesenteric vein were dissected free from the adventitia, cut into segments of approximately 2 mm in length, mounted on muscle holders, and placed into 20 mL organ baths filled with PSS with oxygenation and temperature maintained as above for study under isometric conditions. Optimum preload for each ring was determined with 20 mM KCl followed by a 30 min relaxation period.

Tissues were checked for endothelial competence by contracting the rings with 20 mM KCl (arteries) of 2 $\mu$M phenylephrine (veins) and then challenging with 1 $\mu$M acetylcholine or 20 U thrombin, respectively. A relaxation of at least 65% was considered acceptable. The vessels were then washed free of drugs and allowed to relax for 30 min.

For compound testing, the coronary artery rings were contracted with 50 nM 9,11-dideoxy-11$\alpha$,9$\alpha$-epoxymethano-prostaglandin $PGF_{2\alpha}$ (U46619), and the mesenteric veins were contracted with 2 $\mu$M phenylephrine. These concentrations were chosen to provide approximately 50% of the maximum contraction attainable. Test compounds were added beginning 5 min after the contraction had reached a plateau. Additions were made cumulatively as log doses over the concentration range of 10 nM to 100 μM. Successive doses were added to the bath at 10 min intervals or when the previous response had reached a plateau.

After the last dose of test agent, the tissues were washed repeatedly every 10 min until complete relaxation was obtained. Tissue viability and endothelium competence was then verified by recontracting the vessels with the prostaglandin (arteries) or phenylephrine (veins) and challenging with acetylcholine or thrombin, respectively, as above.

The compounds which exhibited mixed (arterial and venous) vasodilator activity were then tested for their 3'-5'-cyclic guanosine monophosphate phosphodiesterase inhibition (cGMP-PDEI) characteristics. The mode of testing was a modification of the procedure by W. J. Thompson, et al. Those mixed vasodilators with cGMP-PDEI mechanisms should be useful in the treatment of various cardiovascular diseases.

The compounds of the invention which exhibit mixed vasodilator effects and are also cGMP, PDE inhibitors are exemplified by compounds such as 1-phenylmethyl-N-[[4-ethyl-2-(2-ethyl-4-methyl-1H-imidazol-1-yl)]pyrimidin-5-yl]-1H-imidazol-2-carboxamide and 1-phenylmethyl-N-[4-ethyl-2-(1H-imidazol-1-yl)pyrimidin-5-yl]-1H-imidazol-2-carboxamide.

The compounds of the invention which exhibit mixed vasodilator effects but which are not cGMP-PDE inhibitors are exemplified by compounds such as N-(4-ethyl-5-pyrimidinyl)-1H-imidazol-2-carboxamide and N-(4-ethyl-5-pyrimidinyl)-1-ethyl-1H-imidazol-4-carboxamide.

Compounds which exhibit selective coronary artery dilation and very little cGMP-PDE inhibition are exemplified by N-(4-ethyl-5-pyrimidinyl)-1-ethyl-1H-imidazol-4-carboxamide.

Because the compounds exhibit general cardiovascular activity with specific effects, it is envisioned that they would also prove useful in disease states where bronchodilators, anti-allergics, or topical agents for baldness are indicated.

The compounds of the invention can be administered orally or parenterally. The dosage and method of administration will be dependent on the age, weight, sex and other characteristics of the subject to be treated and the disease state or states to be treated. The compounds when administered orally or parenterally will be admixed with non-toxic pharmaceutically acceptable carriers, which may be solid or liquid in nature, in accordance with standard pharmaceutical practices taking into account the compound/s to be administered, the dosage form and disease state/s to be effected.

Preparations of the compounds include solid forms as powders, tablets, dispersible granules, capsules, cachets and suppositories. Liquid form preparations include solutions, suspensions and emulsions. Formulations for topical application would include such forms as creams, aerosols, sprays, powders, lotions, ointments and appliques.

The invention described hereinabove is illustrated below in the Examples which, however, is not to be construed as limiting the invention.

EXAMPLES

EXAMPLE 1

N-(4-Ethyl-5-pyrimidinyl)-1-(phenylmethyl)-1H-imidazol-2-yl-carboxamide 1-(phenylmethyl)-1H-imidazole-2-carboxylic acid (8.2 g, 40.6 mmol) is added at room temperature in portions to thionyl chloride (50 mL) and the reaction mixture is heated at 80° C. for 1 h and subsequently chilled to 0° C. The solid is filtered and washed with ether (100 mL) and dried. The acid chloride thus obtained (5.6 g, 22.3 mmol) is added portion-wise to a solution of 4-ethyl-5-amino-pyrimidine (2.75 g, 22.3 mmol) in pyridine (3.96 mL) and THF (50 mL) at 0° C. Stirring is continued at 0° C. for 10 minutes, then at room temperature for 1 h and 50° C. for 7 h. The reaction mixture is allowed to cool and stirred at room temperature for 13 h. The solution is concentrated in vacuo and the residue is taken up in water. The aqueous layer is then adjusted to pH 8.0 with saturated sodium carbonate solution and extracted with methylene chloride (3×100 mL). The organic extracts are combined, dried (MgSO$_4$) and concentrated in vacuo. Recrystallization from a 1:1 mixture of ether-petroleum ether affords the title compound.

$^1$H NMR (DMSO-d$_6$) δ1.17(t,3H), 2.74(q,2H), 5.70(s,2H), 7.20(s,1H), 7.25-7.34(m,5H), 7.65(s,1H), 8.74(d,1H), 8.97(s,1H) and 10.37(s,1H) ppm.

EXAMPLE 2

In a manner similar to Example 1, the following compounds may be prepared.

A) 1-Phenylmethyl-N-[[4-ethyl-2-(2-ethyl-4-methyl-1H-imidazol-1-yl)]pyrimidin-5-yl]-1H-imidazol-2-carboxamide.

$^1$H NMR (CDCl$_3$) δ1.37(m,6H), 2.25(s,3H), 2.90(q,2H), 3.3(q,2H), 5.75(s,2H), 7.12(s,1H), 7.13(s,1H), 7.28(m,5H), 7.6(s,1H), and 9.25(s,2H) ppm.

B) 1-Phenylmethyl-N-[4-ethyl-2-(1H-imidazol-1-yl)pyrimidin-5-yl]1H-imidazol-2-carboxamide.

$^1$H NMR (CDCl$_3$) δ1.41(t,3H), 2.9(q,2H), 5.75(s,2H), 7.26(m,3H), 7.29(m,5H), 7.89(s,1H), 8.6(s,1H), 9.26(s,1H), and 9.30(s,1H) ppm.

EXAMPLE 3

N-(4-Ethyl-5-pyrimidinyl)-1H-imidazol-2-yl-carboxamide

Small pieces of sodium (~230 mg) are added to a solution of Example 1 (2 g, 6.5 mmol) in freshly distilled ammonia until the blue color persists. The reaction mixture is quenched with a small amount of solid ammonium chloride and allowed to evaporate off excess ammonia. The residue is taken up in 25 mL of water and the pH is adjusted to 7.0 with 18% HCl. This is extracted with methylene chloride (3×50 mL). The organic extracts are combined, dried over MgSO$_4$ and concentrated in vacuo. Recrystallization from methanol and ether (1+19) affords the title compound.

$^1$H NMR (DMSO-d$_6$) δ1.21(t,3H), 2.80(q,2H), 7.19(s,1H), 7.42(s,1H), 8.77(d,1H), 8.98(s,1H), 10.33(s,1H), and 13.35(s,1H) ppm.

EXAMPLE 4

N-[[4-Ethyl-2-(2-ethyl-4-methyl-1H-imidazol-1-yl)]pyrimidin-5-yl]-1H-imidazol-2-carboxamide In a manner similar to Example 3, 1-phenylmethyl-N-[[4-ethyl-2-(2-ethyl-4-methyl-1H-imidazol-1-yl)]pyrimidin-5-yl]-1H-imidazol-2-carboxamide is reacted to provide the titled compound.

$^1$H NMR (DMSO-d$_6$) δ1.26(m,6H), 2.13(s,3H), 2.84(q,4H), 3.2(q,4H), 7.2(s,1H), 7.4(s,1H), 7.6(s,1H), 8.8(s,1H), 10.3(s,1H) and 13.34(brs,1H) ppm.

EXAMPLE 5

N-(4-Ethyl-5-pyrimidinyl)-1-ethyl-1H-imidazol-4-carboxamide

A solution of 1-ethyl-1H-imidazole-4-carboxylic acid (2.5 g, 17.8 mmol) and thionyl chloride (65 mL) is refluxed for 1.5 h. The thionyl chloride is removed in vacuo using toluene to azeotrope thionyl chloride. To a suspension of the residue is added THF (60 mL) and pyridine (3.2 mL, 39.2 mmol), followed by 4-ethyl-5-pyrimidineamine (2.2 g, 17.8 mmol). The reaction mixture is refluxed for 17 h, and concentrated in vacuo. The residue is taken up in water (100 mL), and the pH of the solution is adjusted to 8.0 by the addition of solid potassium carbonate. The aqueous layer is extracted with methylene chloride (3×100 mL). The organic extracts are combined, dried over MgSO$_4$ and concentrated in vacuo. The residue is chromatographed on silica gel (300 g) using 3% MeOH in CH$_2$Cl$_2$ as eluent. The product fractions are combined and the solvent removed. The resultant material is triturated with ether+MeOH (19+1) to give the title compound.

$^1$H NMR (CDCl$_3$) δ1.39(t,3H), 1.51(t,3H), 2.90(q,2H), 4.08(q,2H), 7.49(s,1H), 7.71(s,1H), 8.94(s,1H), 8.96(brs,1H) and 9.49(s,1H) ppm.

EXAMPLE 6

1-Ethyl-N-[[4-ethyl-2-[2-ethyl-4-methyl-1H-imidazol-1-yl)]pyrimidin-5-yl]-1H-imidazole-4-carboxamide In a manner similar to Example 5, the title compound was prepared.

$^1$H NMR (CDCl$_3$) δ1.32(t,3H), 1.38(t,3H), 1.50(t,3H), 2.25(t,3H), 2.9(q,2H), 3.28(q,2H), 4.09(q,2H), 7.49(s,1H), 7.56(s,1H), 7.71(s,1H), 8.9(s,1H) and 9.34(s,1H), ppm.

EXAMPLE 7

2-(2-Ethyl-4-methyl-1H-imidazol-1-yl)-4-ethyl-5-nitropyrimidine

A suspension of lithium t-butoxide (5.2 g, 65 mmol) in anhydrous THF (150 mL) is treated with cuprous iodide (12.4 g, 65 mmol) at room temperature under a nitrogen atmosphere and stirred for 1 h. The mixture is cooled to −78° C., treated with 2M ethylmagnesium bromide (32.5 mL, 65 mmol) and stirred for 20 min. A pre-cooled solution (−78° C.) of 2,4-dichloro-5-nitropyrimidine (9.7 g, 50 mmol) in THF (30 mL) is added via canula. The mixture is stirred for 2 h at −78° C. then a 1:1 mixture of saturated aqueous solution of NH$_4$Cl and ether (1000 mL) is added and stirred for 1 h. The reaction mixture is extracted with ether (2×200 mL). The organic phase is washed with 50 mL of 1N HCl, followed by saturated NaHCO$_3$ and brine. Drying over MgSO$_4$ and concentration in vacuo is followed by flash column chromatography on silica gel which affords material to which is added 20 mL acetonitrile then a solution of 2-ethyl-4-methyl imidazole (5.4 g, 49 mmol) in acetonitrile (40 mL). The mixture is allowed to stir for 15 h at room temperature. The solvent is evaporated and the solid is subjected to flash chromatography on silica gel with CH$_2$Cl$_2$:MeOH (19+1) as eluent to afford the title compound.

$^1$H NMR (CDCl$_3$) δ1.36(t,3H), 1.42(t,3H), 2.24(s,3H), 3.26(m,4H), 7.63(s,1H), 9.24(s,1H), ppm.

EXAMPLE 8

4-Ethyl-2-(1H-imidazol-1-yl)-5-nitropyrimidine

The title compound is prepared in a manner similar to that described in Example 7.

$^1$H NMR (CDCl$_3$) δ1.43(t,3H), 3.27(q,2H), 7.19(s,1H), 7.91(s,1H), 8.65(s,1H) and 9.26(s,1H) ppm.

EXAMPLE 9

4-Ethyl-2-(2-ethyl-4-methyl-1H-imidazol-1-yl)pyrimidineamine

To a solution of the product of Example 7 (1.1 g, 4.2 mmol) is 15 mL of ethanol is added tin chloride dihydrate (4.8 g, 10 mmol) in small portions at 0° C. for 30 min. The mixture is then stirred with methylene chloride (40 mL) and 1N sodium hydroxide (20 mL). The aqueous fraction is extracted with methylene chloride (2×50 mL). The organic phases are washed with brine, dried over MgSO$_4$ and concentrated in vacuo to afford the title compound.

$^1$H NMR (CDCl$_3$) δ1.33(m,6H), 2.23(s,3H), 2.68(q,2H), 3.18(q,2H), 3.82(s,2H), 7.41(s,1H) and 8.0(s,1H) ppm.

EXAMPLE 10

4-Ethyl-2-(1H-imidazol-1-yl)-5-pyrimidineamine

The title compound is prepared in a manner similar to Example 9.

$^1$H NMR (CDCl$_3$) δ1.36(t,3H), 2.7(q,2H), 3.72(s,2H), 7.12(s,1H), 7.82(s,1H), 7.99(s,1H) and 8.5(s,1H) ppm.

EXAMPLE 11

N-Bis-[(1-ethyl-1H-imidazol-4-yl)-carbonyl]-4-ethyl-2-(1H-imidazol-1-yl)-5-pyrimidineamine The title compound is obtained in a method similar to Example 5, substituting equal molar amounts of triethylamine for pyridine.

$^1$H NMR (CDCl$_3$) δ1.31(t,3H), 1.43(t,3H), 1.53(t,3H), 2.92(q,2H), 4.1(q,2H), 4.2(br s,2H), 7.16(s,1H), 7.27(s,1H), 7.61(s,1H), 7.62(s,1H), 7.89(s,1H), 8.14(s,1H), 8.4(br s,1H), and 8.6(s,1H) ppm.

EXAMPLE 12

N-Bis-[(1-ethyl-1H-imidazol-4-yl)carbonyl]-4-ethyl-2-(2-ethyl-4-methyl-1H-imidazol-1-yl)-5-pyrimidine The title compound is obtained in a method similar to Example 5 substituting equal molar amounts of triethylamine for pyridine.

$^1$H NMR (CDCl$_3$) δ1.33(t,3H), 1.35(t,3H), 1.43(t,3H), 1.53(t,3H), 2.25(s,3H), 2.91(q,2H), 3.26(q,2H), 4.08(q,2H), 4.2(br s,2H), 7.27(s,1H), 7.54(s,1H), 7.60(s,1H), 7.63(s,2H) and 8.15(s,1H) ppm.

I claim:

1. A compound of the following formula I:

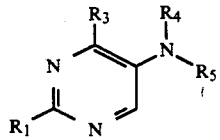

wherein,

R₁ is hydrogen or

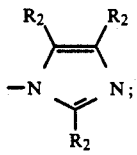

$R_2$ are the same or independently hydrogen or lower alkyl;

$R_3$ is hydrogen or lower alkyl;

$R_4$ is

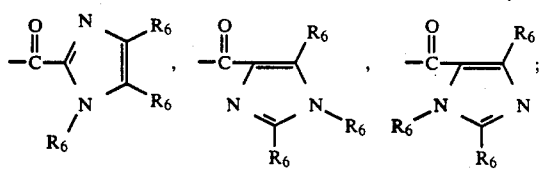

$R_5$ is hydrogen or $R_4$ and $R_6$ are the same or independently hydrogen, lower alkyl or benzyl.

2. A compound of claim 1 which is 1-ethyl-N-[[4-ethyl-2-[2-ethyll-4-methyl-1H-imidazol-1-yl]]pyrimidin-5-yl]-1H-imidazole-4-carboxamide.

3. A compound of claim 1 which is 1-phenylmethyl-N-[[4-ethyl-2-(2-ethyl-4-methyl-1H-imidazol-1-yl)]pyrimidin-5-yl]-1H-imidazol-2-carboxamide.

4. A compound of claim 1 which is N-[[4-ethyl-2-(2-ethyl-4-methyl-1H-imidazol-1-yl)]-pyrimidin-5-yl]-1H-imidazol-2-carboxamide.

5. A compound of claim 1 which is 1-phenylmethyl-N-[4-ethyl-2-(1H-imidazol-1-yl)pyrimidin-5-yl]-1H-imidazol-2carboxamide.

6. A compound of claim 1 which is N-bis-[(1-ethyl-1H-imidazol-4-yl)carbonyl]-4-ethyl-2-(2-ethyl-4-methyl-1H-imidazol-1-yl)-5-pyrimidine.

7. A compound of claim 1 which is N-bis-[(1-ethyl-1H-imidazol-4-yl)carbonyl]-4-ethyl-2-1H-imidazol-1-yl)-5-pyrimidineamine.

8. A compound of claim 1 which is N-(4-ethyl-5-pyrimidinyl)-1-(phenylmethyl)-1H-imidazol-2-yl-carboxamide.

9. A compound of claim 1 which is N-(4-ethyl-5-pyrimidinyl)-1H-imidazol-2-yl-carboxamide.

10. A compound of claim 1 which is N-(4-ethyl-5-pyrimidinyl)-1-ethyl-1H-imidazol-4-carboxamide.

11. A pharmaceutical composition comprising an effective amount of at least one compound according to claim 1, together with one or more non-toxic pharmaceutically acceptable carriers.

* * * * *